United States Patent [19]
Sherman

[11] Patent Number: 5,593,569
[45] Date of Patent: Jan. 14, 1997

[54] HYDROCRACKING PROCESSES USING A HOMOGENOUS CATALYSIS SYSTEM COMPRISING A METAL HALIDE LEWIS ACID, A BRONSTED ACID AND AN ALKANE

[75] Inventor: Larry G. Sherman, Edmond, Okla.

[73] Assignee: Kerr-McGee, Oklahoma City, Okla.

[21] Appl. No.: 370,056

[22] Filed: Jan. 9, 1995

[51] Int. Cl.$^6$ .................................................. C10G 47/02
[52] U.S. Cl. .......................... 208/108; 585/374; 585/707; 585/747; 208/111
[58] Field of Search ...................... 205/108, 111; 585/374, 707, 747

[56] References Cited

U.S. PATENT DOCUMENTS

| | | | |
|---|---|---|---|
| 3,847,795 | 11/1974 | Rieve et al. | 208/100 |
| 3,957,628 | 5/1976 | Siskin et al. | 208/254 |
| 4,043,900 | 8/1977 | Siskin | 208/216 |
| 4,058,575 | 11/1977 | Cahn et al. | 208/108 |
| 4,120,912 | 10/1978 | Hulme | 260/666 P |
| 5,406,018 | 4/1995 | Sherman | 585/727 |

*Primary Examiner*—Helane Myers
*Attorney, Agent, or Firm*—Herbert M. Hanegan; J. Rodgers Lunsford, III

[57] ABSTRACT

A process of converting high molecular hydrocarbon feedstock into lower molecular weight components in the presence of a homogenous catalysis system is disclosed. The catalysis system comprises a catalyst complex formed by the interaction of a metal halide-type Lewis acid, a protic Bronsted acid or Bronsted acid donor and a fluid hydrocarbon selected from a $C_2$-$C_{14}$ alkane dissolved in a fluid hydrocarbon. The homogeneous catalysis system can be produced as a liquid phase or a supercritical fluid solution. The process is especially useful where the hydrocarbon feedstock consists of deasphalted oil or mixed paraffins. The hydrocrackate, especially that derived from paraffin feedstocks, has a carbon number distribution equivalent to that of the fluid hydrocarbon of the catalyst complex.

15 Claims, 2 Drawing Sheets

Fig_1

Fig. 2

HYDROCRACKING PROCESSES USING A HOMOGENOUS CATALYSIS SYSTEM COMPRISING A METAL HALIDE LEWIS ACID, A BRONSTED ACID AND AN ALKANE

BACKGROUND OF THE INVENTION

1. Field of the Invention

The invention is drawn to processes for the catalyzed pyrolysis (or "hydrocracking") of hydrocarbon feedstocks in the presence of hydrogen which use a homogenous catalysis system. The catalysis system consists of a complex of a metal halide Lewis acid, a Bronsted acid and a fluid hydrocarbon dissolved in a second fluid hydrocarbon. The fluid hydrocarbon comprises a $C_2$-$C_{14}$ alkane.

2. Description of the Prior Art

Hydrocracking refers to a class of processes in which larger molecules are cracked to form smaller molecules in the presence of a catalyst and hydrogen. Hydrocracking processes are particularly useful in the treatment of purified distillate fractions of crude oil.

Crude oils are generally classified according to properties of either the atmospheric distillation tower bottoms (650° F.+) or vacuum distillation tower bottoms (1,050° F.+). For instance, the atmospheric distillation tower bottoms of "light crudes" have less than 5% carbon residue (as defined by destructive distillation in a Conradson Carbon test) and less than 10–15 weight parts per million (wppm) nickel and vanadium. Such feeds can be run directly to a catalytic cracking reactor.

Heavy crudes typically contain 70–85% (vol) of 650° F.+ residue. Such residual oils contain high volumes of carbon residue and are thus regarded as distress stocks by the petroleum industry. The presence of the carbon residue contributes to the production of coke during cracking operations. In addition, high levels of metals in the heavy ends rapidly deactivate the cracking catalyst, leading to uneconomic yields. Thermal processing (such as coking) or, alternatively, deasphalting is therefore normally required to reduce the carbon residues, along with the metals, prior to further upgrading. In addition to being highly contaminated, heavy crudes contain a limited amount of valuable light products such as gasoline and kerosene.

It has long been recognized that solid catalysts, such as $AlCl_3$ (and more particularly $AlCl_3$ promoted by HCl), are effective in catalyzing the cracking of a wide variety of hydrocarbons to predominantly lighter hydrocarbons. Catalytic hydrocracking methods are well known and typically are conducted over such solid catalysts at temperatures of 500°–800° F. at pressures of 1000–2000 psi and holding times of 1–3 hours. Two well known types of hydrocracking are the single-stage type and the two-stage type. In the former process, the feedstock is pretreated to remove essentially all sulfur and nitrogen. The hydrocarbon stream is then pyrolyzed in a reactor in the presence of a solid catalyst and hydrogen at a single pass conversion of between 40 and 70 percent. In the two-stage process, a second stage uses the effluent from the single-stage type hydrocracking process (after elimination of the bulk of the sulfur and nitrogen as $H_2S$ and $NH_3$, respectively) and a second hydrocracking reactor. The unconverted feedstock is recycled in the second hydrocracking reactor. Because the catalyst in the second hydrocracking reactor operates in an essentially ammonia-free environment, the extent of conversion in this reactor is at a higher level, e.g., 60 to 80 percent per pass.

It is generally recognized that the solid catalyst in such hydrocracking processes reduces the requisite temperature needed for the reaction. In addition, it promotes the hydrogenation of the cracked products ("hydrocrackate") and dictates the selectivity of cracking.

The hydrocracking processes of the prior art unfortunately render heavy polymers as by-products. These, in turn, produce coke on the solid catalyst. In addition, the processes must be conducted under rather severe operating conditions as noted above. There is an emerging need for improved hydrocracking processes which are not limited by metal buildup and undesirable catalyst coking. Improved hydrocracking processes are further desired which require milder operating conditions and which minimize undesirable low-value process by-products.

Further, there is a tremendous economic interest in developing hydrocracking processes which are suitable for the production of n-paraffins having a specified carbon number, such as, for example, dodecane.

Hydrocracking of high molecular weight paraffin feedstocks, such as hexadecane (cetane), has been extensively studied. Goldfarb et al., (*Kinetics and Catalysis*, Vol. 22, No. 3, Part 2, pp. 507–513) reported high conversion over a supported NiMo catalyst at 900° F. with a holding time of 40 min. White et al., (*Journal of Physical Chemistry*, Vol. 68, No. 10, October, 1964, pp. 3085–86) reported 50% conversion at 550° F., 1200 psi, and a holding time of 8 seconds in the presence of a sulfided Ni on silica alumina catalyst. Flinn et al., at Gulf Research (*Industrial and Engineering Research*, Vol. 52, No. 2, February 1960, pp. 153–156) reported virtually complete reaction with a sulfided 3 wt% Ni catalyst on silica alumina at 702° F., 980 psi and a holding time of about 1 hour.

Unfortunately, the hydrocracking catalysts of the prior art employed with paraffin feedstocks render a hydrocrackate of a wide range of carbon numbers; typically having a preponderance of light ends. For instance, the data from the referenced studies on sulfided $Ni/SiO_2$-$Al_2O_3$ catalysts demonstrate a broad $C_3$-$C_{13}$ product distribution at low conversion. Simpler product distribution is obtained at 100% conversion. In the latter, the product is 80 wt% $C_5$ with the balance being predominantly $C_6$. The product distribution is consistent with the following reaction network:

Two reaction pathways (likely involving two distinct sites) occur on sulfided Ni on $SiO_2$-$Al_2O_3$ catalyst. Path A (which likely involves a weak acid site) involves breaking the $C_{16}$ fragment into two $C_8$ fragments which, in turn, rapidly crack to yield either $C_4$ or $C_3$ and $C_5$ fractions. Path B (likely involving a stronger acid site) produces $C_6$ and $C_4$ fragments. The small fragments do not leave as butane but rather recombine to produce a $C_8$ fragment which is then fed into the $C_8$ cracking network. Selectivity between Paths A and B is approximately 50/50.

Hexadecane crackings has also been studied using hydrogenation catalysts such as platinum on silica-alumina.

Unlike the acidic catalysts (which produce about 80% $C_5$) the non-acidic catalysts tend to produce an equimolar mixture of $C_4$, $C_5$, $C_6$ ... $C_{12}$. See, for example, Coonradt and Garwood (*Industrial & Engineering Chemistry, Process Design and Development*, 1964, No. 3, p. 38). A need exists therefore for a hydrocracking process for use with heavy paraffinic feedstocks which is capable of selectively rendering a desired hydrocrackate of a specified carbon number instead of a range of carbon numbers.

SUMMARY OF THE INVENTION

The invention relates to the application of a homogenous catalysis system in the hydrocracking of high molecular weight hydrocarbon feedstocks. The catalysis system comprises a $C_2$–$C_{14}$ alkane fluid hydrocarbon (as solvent) and a catalyst complex which is formed by the interaction of a hydrocarbon, a metal halide-type Lewis acid and a protic Bronsted acid or Bronsted acid donor. It is desirable that the protic acid have an anion corresponding to the anionic component of the Lewis acid. The hydrocarbon employed in the catalyst complex is most preferably paraffinic. The homogeneous catalysis system can be produced as either a liquid phase solution or a supercritical fluid solution. As a result of the creation of the homogenous catalysis system (comprising the catalyst complex dissolved in the $C_2$–$C_{14}$ alkane), the process operates at temperatures, pressures and holding times much lower than the hydrocracking processes of the prior art.

The hydrocracking processes of this invention proceed rapidly at temperatures between about 400° and 850° F. with high selectivity and at high conversion. Commercially, the invention has wide applicability in the generation of lower molecular weight paraffinic hydrocarbons, from heavier, less valuable feedstocks, such as purified distillates of heavy crude. In addition, the superacid catalysis system has particular applicability in the hydrocracking of feedstocks containing high molecular weight paraffins. The hydrocrackate derived from paraffinic feedstocks has a carbon number distribution equivalent to that of the hydrocarbon in which the catalyst complex is dissolved. At 100% conversion, the hydrocrackate further contains minimal light and heavy end carbon fragments. One potentially useful application of this invention is the selective conversion of diesel oil to solvent-grade hexane.

DETAILED DESCRIPTION OF THE PREFERRED EMBODIMENTS

The invention relates to processes of converting a high molecular weight hydrocarbon feedstock to lower molecular weight components in a homogeneous catalysis system. In particular, the invention relates to a method of hydrocracking hydrocarbon feedstocks in such catalysis systems.

The catalysis system comprises two components—a catalyst complex and a non-complexed hydrocarbon in which the catalyst complex is diluted. The catalyst complex is the reaction product of a Lewis acid, a Bronsted acid or Bronsted acid donor and a hydrocarbon. The hydrocarbon of the catalyst complex and the non-complexed hydrocarbon may be of the same chemical constituency. Such hydrocarbons, typically fluid, are preferably either a $C_2$–$C_{14}$ alkane or isoalkane. In a preferred embodiment, the first and second hydrocarbons are paraffin and further are of the same chemical species.

The fluid hydrocarbon, which is combined with the Lewis acid and Bronsted acid, has two functions. First, it serves as a reactant with the Lewis acid and Bronsted acid or acid donor to form the catalyst complex. Second, since it is present in excess of that needed to stoichiometrically complex with the Lewis acid and Bronsted acid or donor, it serves as a solvent for the resultant catalyst complex. The catalyst complex is further diluted with hydrocarbon.

In one embodiment of this invention, hydrocarbon is first added to the Lewis acid to form a complex. An amount of hydrocarbon stoichiometrically in excess of that required to form the catalyst complex is then added along with the Bronsted acid or Bronsted acid donor. The catalyst complex is formed and, by the excessive hydrocarbon present, the catalyst complex is solubilized by the non-complexed hydrocarbon. The result is the catalysis system. Optionally, additional hydrocarbon may be added to further dilute the catalysis system. In this embodiment, the hydrocarbon initially added ("the (first) hydrocarbon") and the hydrocarbon added in a stoichiometric excess ("the (second) hydrocarbon") are preferably of the same chemical species. The optionally added hydrocarbon is further normally considered a part of the (second) hydrocarbon.

In a second embodiment of this invention, a (first) hydrocarbon is added to the Lewis acid. Often, the Bronsted acid or Bronsted acid donor may be concurrently added. The amount of resultant catalyst complex is then diluted with the (second) hydrocarbon. The first and second hydrocarbon may or may not be of the same chemical species.

Higher molecular weight feedstocks may be subjected to the hydrocracking process of this invention. Particularly good results are obtained when the feedstock is purified from a heavy crude oil or consists of mixed heavy paraffins.

The term "crude oil feedstock" is used herein to denote the full range of crude oils from primary, secondary or tertiary recoveries of conventional or offshore oil fields and to the myriad of feedstocks derived therefrom. "Crude oil feedstocks" may also be "syncrudes" such as those that can be derived from coal, shale oil, tar sands and bitumens. The crude oil feedstock may be virgin (straight run) or generated synthetically by blending.

Such crude oil feedstocks should be treated by traditional methods prior to being subjected to the hydrocracking process of this invention. Such pre-treatment steps serve to remove those components which may be detrimental to the efficacy of hydrocracking processes. For example, the crude oil feedstock should be desalted prior to use since sodium chloride is known to be a poison in many hydrocracking operations. Alternatively, the feedstock could be distilled and the bottoms fraction deasphalted prior to hydrocracking in order to concentrate refractory asphaltenes and metals and eliminate them from the hydrocracking feed. Such byproduct streams are then gasified to produce energy and ash. The deasphalted oil is then subjected to the hydrocracking process of this invention.

A particularly desirable feedstock for use in this invention is one containing a mixture of heavy paraffins generally derived from fuel value residual hydrocarbon feedstocks. Typically, such heavy paraffins consist of those having a $C_{14}$–$C_{35}$ backbone. Fuel value residual hydrocarbon feedstocks are those residua, common to almost all petroleum refining, which remain after the more useful lighter and middle distillates have been removed from the crude.

In accordance with this invention, conversion of the high molecular weight hydrocarbon feedstock is carried out with a homogenous catalysis system which consists of the catalyst complex and a (second) hydrocarbon. The homogenous medium may be in a liquid state or a supercritical fluid. The feedstock need not be soluble in the homogenous medium.

The Fluid of the Reaction Medium

The hydrocarbon used in the production of the catalyst complex as well as the hydrocarbon used to dilute the catalyst complex are both preferably fluid and most preferably paraffinic. Such hydrocarbons may be composed of a $C_2$–$C_{14}$ (most preferably $C_6$–$C_{12}$) n- or i-alkane. The preferred alkanes are hexane, octane, decane and dodecane.

While the (first) fluid hydrocarbon and the (second) fluid hydrocarbon are of the same chemical species in a preferred embodiment of this invention, there is no requirement that this be the case.

Compounds in the feedstream which are capable of being readily converted to higher molecular weight materials by thermal or catalytic polymerization may be first rejected using a $C_2$–$C_{14}$ hydrocarbon of the above paragraph which selectively extracts the desired compounds.

Ideally, the (second) fluid hydrocarbon employed in the process of this invention should be one which corresponds to the desired product(s) in the hydrocrackate. This is especially true when the hydrocarbon feedstock consists of one or a mixture of high molecular weight paraffins. This phenomena may be referred to as "molecular templating" since it reflects the fact that the soluble complex catalyst templates the chemistry of the hydrocrackate to emulate the fluid hydrocarbon in which it is dissolved. For instance, where the desired end products are those containing $C_6$ fragments, the (second) fluid hydrocarbon chosen for use as the solvent for diluting the catalyst complex should be a $C_6$ hydrocarbon.

The mechanism which is attributed to such templating is not certain. It is believed however that it occurs from the bonding of the cracked fragments to the catalyst complex. When the hydrocrackate approaches the carbon number of the (second) fluid hydrocarbon, hydride transfer from the (second) fluid hydrocarbon liberates the hydrocrackate. Although not necessarily energetically favored, the liberation step is believed to be driven by mass action since the vast majority of molecules surrounding the catalyst are of the (second) fluid hydrocarbon. This is especially true when the first and second fluid hydrocarbons are of the same chemical species.

Supercritical Fluids

The homogenous catalysis system may be formed as a supercritical fluid. A supercritical fluid is not a liquid, nor does it exhibit the properties of a gas; instead it exhibits solubility properties more like that of a liquid than a gas, and molecular diffusion properties more like that of a gas than a liquid; hence it is referred to in the art as a "supercritical fluid."

For purposes of this invention the supercritical fluid may be comprised of fluid hydrocarbons which under normal conditions of temperature and pressure would be normally liquid components or a mixture of normally liquid and normally gaseous components. In the first situation wherein the fluid hydrocarbons of the supercritical fluid are normally liquid components, the components are elevated in temperature above the critical temperature of the mixture and maintained under a pressure sufficient to produce a fluid phase of a density at least 0.1 times that of the pure component when saturated in its liquid state at 68° F. (20° C.).

In the second situation, the fluid hydrocarbons of the catalysis system comprise a mixture of a normal liquid and a normal gas, the gas component functions as a "solvent" for the liquid such that the mixture has a lower critical temperature than does the liquid component alone. As a consequence the liquid-gas mixture can be formed into a supercritical fluid at lower temperatures than could the liquid component alone.

The use in the catalysis system of a solvent in combination with the fluid hydrocarbons allows the supercritical fluid state to be reached at lower temperatures. For instance, in the absence of a solvent a temperature exceeding 300° F. is needed to transform n-butane from a liquid phase to a supercritical fluid. With the use of a solvent such as propane, a mixture is produced which can be rendered into a supercritical fluid at temperatures of 200° F or less.

The "solvent" (hereinafter "inert solvent") may be any polar or non-polar, inert solvent known to have a critical temperature between about −110° and 400° F. (−79° and 204° C.). These solvents include methane, ethane, propane, sulfur dioxide, carbon dioxide, nitrogen oxides (e.g. $N_2O_3$, NO, $NO_2$), the low molecular weight fluorocarbons, or halocarbons, the rare gas elements (argon or xenon), and the like. By inert, it is meant that the solvent does not reactively interfere in the formation of the catalyst or the hydrocracking process to yield a separate product. The preferred solvent includes ethane, propane and carbon dioxide.

In the context of this invention, the "solvent" primarily serves as the component of the supercritical mixture which provides the mixture with the pressure and temperature properties most preferred for the reaction in the supercritical state. This supercritical state allows both the formation and the solubilization of the catalyst complex into the homogeneous catalysis system.

"Supercritical conditions" thus refer to conditions where the temperatures are above the critical temperature of the fluid hydrocarbons and a pressure sufficient to impart a density to the mixture which is at least equal to 0.1 of the density of the fluid hydrocarbons when saturated in their liquid state, at 68° F. Preferably, the density of the mixture should be greater than about 0.25 times the density of the fluid hydrocarbons in their liquid state at 68° F. (20° C.). In general, a supercritical pressure will be in the range of about 600 to about 5,000 psi; preferably from about 700 to about 2,500 psi.

Liquid Phase Fluids

The homogenous catalysis system may, as an alternative, be formed in the liquid phase. When liquid phase reaction conditions are selected for the practice of this process, the fluid hydrocarbon is most preferably a $C_6$–$C_{12}$ n- or i-alkane.

In the case of a liquid phase reaction, the (first) and (second) fluid hydrocarbons will be maintained at a temperature below their critical temperature and under a pressure sufficient to maintain the hydrocarbons in the liquid state while forming the catalyst complex.

Accordingly, when forming the catalyst complex or conducting the hydrocracking process, the temperature may not exceed the critical temperature of the (first) fluid hydrocarbon. Thus, for hexane the temperature within the cracking reactor should not exceed 454° F. (235° C.).

Choice of Fluid Type

The choice of the fluid hydrocarbon as a liquid phase or as a supercritical fluid results in different operating economics. Generally, in a supercritical fluid medium, hydrocracking proceeds at lower temperatures and at higher rates than in liquid phase fluids. Following the reaction, the catalyst complex can readily be separated from the fluid hydrocarbons/solvent components of the supercritical fluid by changing the density of the supercritical fluid. Decreasing the density precipitates the catalyst complex from solution. The density may be decreased either by increasing the temperature or by lowering the pressure of the supercritical fluid, or by a combination of both. This involves a need for reheating and/or recompression of the unreacted feedstream for recycle use, the cost of which may lead one to prefer a liquid phase reaction procedure.

In a liquid phase procedure, the reaction medium may be allowed to undergo flash evaporation to separate the lower molecular weight components from the catalyst complex. Again the unreacted feed and non-reacted (first) fluid hydrocarbon, if any, and (second) fluid hydrocarbon are recovered and recompressed—but to a lesser degree than required for supercritical operations—at a reduced recompression cost. As used herein, the term "total non-reacted hydrocarbon" shall refer to the non-reacted (first) fluid hydrocarbon and (second) fluid hydrocarbon.

The Catalyst

The invention provides a homogeneous catalysis system for the cracking of hydrocarbon feedstocks. The catalyst complex is the product of reaction of at least (a) a Lewis acid of the formula $R_{(m-2-z)}MX_{2+z}$ wherein M is a Group 3a, 5a or 5b metal, X is a halide, R is a hydrocarbyl radical having 2 to 14 carbon atoms, "m" is an integer equal to the greatest oxidation state of M, and "z" is an integer of 0, 1 or m–2; (b) a Bronsted acid, such as a hydrogen halide, or a Bronsted acid donor, such as an alkyl chloride; and (c) a (first) fluid hydrocarbon selected from alkanes having 14 or fewer carbon atoms. All group references herein are with respect to the Periodic Table of Elements as published in *CRC Handbook of Chemistry and Physics,* 51st Edition (1970–71) published by The Chemical Rubber Co. The catalyst complex is solubilized by the (first) fluid hydrocarbon which does not react or complex with the Lewis acid and hydrogen halide.

The useful Lewis acids include, for example, aluminum trihalides, alkylaluminum dihalides, aluminum oxychlorides, gallium trihalides, alkylgallinium dihalides, boron trihalides, antimony pentahalides, tantalum pentahalides, and niobium pentahalides and the like. Of these, the fluorides of antimony, tantalum, niobium and boron are preferred while for aluminum and gallium the chlorides are preferred. Most preferred as the Lewis acid component for the catalysts are chlorides of aluminum, such as aluminum trichloride, an alkylaluminum monochloride or alkylaluminum dichloride wherein the alkyl group has from 2 to 14 carbon atoms. A particularly preferred Lewis acid is aluminum trichloride.

The Bronsted acids include the protic Bronsted acids that have an anion corresponding to the anion of the Lewis acid used. Thus, the Bronsted acid may be a hydrogen halide selected from hydrogen fluoride, hydrogen chloride, hydrogen bromide and hydrogen iodide. The preferred Bronsted acids are HCl and HBr. Since the most preferred Lewis acid is an aluminum chloride, the most preferred Bronsted acid is hydrogen chloride.

The Bronsted acid may further be supplied in the form of a Bronsted acid donor, namely a compound which at the temperature conditions for formation of the catalyst complex decomposes to yield a Bronsted acid. Such Bronsted acid donors are alkyl chlorides, like butyl chloride, which decomposes into butene and hydrogen chloride.

The homogeneous catalysis system contains the catalyst complex diluted in the (second) fluid hydrocarbon and can be formed in a variety of ways. The (first) fluid hydrocarbon of the catalyst complex can be brought into contact with a source of acid simultaneously while contacting it with a Bronsted acid or Bronsted acid donor. The fluid hydrocarbon is then removed from further contact with the solid Lewis acid complex to produce a homogeneous fluid solution of the two components. The (first) fluid hydrocarbon may be further brought into contact with a source of solid catalyst by flowing the fluid through a bed of a solid Lewis acid, such as $AlCl_3$ to cause Lewis acid to dissolve in the fluid. The (first) fluid hydrocarbon is then removed from further contact with the solid Lewis acid. Thereafter, a Bronsted acid or a Bronsted acid donor may be added to the fluid containing the dissolved Lewis acid. The catalyst forms upon addition of the Bronsted acid. When a Bronsted acid donor, such as an alkyl halide, is added, the catalyst complex forms when the fluid reaches a temperature at which the alkyl chloride ionizes in the presence of the Lewis acid. The alkyl halide is of the formula RX wherein R is a $C_2$–$C_{14}$ alkyl group and X is either —Cl or —Br. Butyl chloride is frequently used because of ease of handling.

In a preferred embodiment, the Lewis acid is solubilized by the (first) fluid hydrocarbon before adding the Bronsted acid or Bronsted acid donor. The preferred ratio of Bronsted acid or Bronsted acid donor to the Lewis acid halide is between 0.5 and 1.5 on a molar basis.

If desired, the activity of the catalysis system may be modified by forming it in the presence of a transition metal halide wherein the transition metal is selected from Group 1b, 6b, 8b and 8 of the Periodic Table of Elements and is a metal which is able to undergo redox reactions. Silver chloride, copper chloride and zirconium chloride are examples of preferred transition metal halides which are useful for modifying the activity of the catalyst. When a transition metal halide modifier is employed, it is preferred to add it to the solubilized Lewis acid in an amount which provides for a molar ratio of transition metal halide to the dissolved Lewis acid of from about 0.5 to about 1.0.

The catalyst complex may be represented by the following formula:

wherein "Cat" is a carbocation, R is a hydrocarbyl radical having from 2 to 14 carbon atoms, M is a group 3a, 5a, or 5b metal or metalloid, X is halide, "m" is an integer equal to the greatest oxidation state of M, "z" is 0, 1, or m–2, and "a" is a number greater than 0.5 and less than 1.5. The carbocation is principally formed by hydrogen abstraction from the fluid hydrocarbon. Where a Bronsted acid donor is employed, the carbocation may further represent the decomposition hydrocarbon, such as butene with the Bronsted acid donor butyl chloride. Accordingly, when forming this catalyst the Bronsted acid halide (HX) should be added to the dissolved Lewis acid ($R_{m-2-z}MX_{2+z}$) in an amount that provides a molar ratio of Bronsted acid halide to Lewis acid of 1:2 to 3:2.

Formation of the Homogeneous Reaction Medium

The homogenous catalysis system is typically prepared by passing the (first) fluid hydrocarbon through a bed of Lewis acid catalyst at approximately 200° F. A second stream of (first) fluid hydrocarbon additionally containing a Bronsted acid donor is then added to yield a catalyst concentration of about 7,000 mol ppm. The catalyst complex is then diluted with a (second) hydrocarbon which may either be a $C_2$–$C_{14}$ n- or i-alkane or one of the polar or non-polar, inert solvents referenced above or a combination thereof. Preferably, the (first) and the (second) fluid hydrocarbon are the same chemical species.

The catalysis system, feedstream and hydrogen are then permitted to flow into the conversion reactor. The catalyst complex, dissolved in the (second) hydrocarbon, precludes the fouling problems often associated with solid catalysts.

The content of catalyst complex dissolved in the total non-reacted hydrocarbon, expressed as the Lewis acid content, may range from about 5.0 to about 50 millimoles of Lewis acid/1000 g of hydrocarbon, preferably from about 5.0 to 40 millimoles/1000 g of hydrocarbon, and more preferably about 30 millimoles/1000 g of hydrocarbon.

The nature of the fluid phase as a liquid phase or as a supercritical fluid may require different methods for forming the homogeneous reaction medium. When liquid phase operation is selected the catalyst complex can be formed in a greater variety of ways than when a supercritical fluid operation is selected.

Supercritical Fluid Operation

The discrete catalyst complex is desirably produced in such a concentration that it remains soluble in the supercritical fluid. Thus, the catalyst complex may be produced in the range from about 400 to about 4,000 ppm, preferably about 1,000 to about 3,000, most preferably about 2,000 ppm, based on the total non-reacted hydrocarbon. Such hydrocarbons are non-complexed. A "non-reacted hydrocarbon" includes the inert solvent, where employed. Desirably, the Bronsted acid should be present in a molar ratio with respect to the Lewis acid ranging from 0.5 to 1.5, preferably about 0.9 to 1.5, and most preferably 1.0 to 1.5.

In its supercritical fluid state the total non-reacted hydrocarbon is desirably characterized as having a $C_2$–$C_{14}$ i- and n-alkane:inert solvent molar ratio of from about 1:99 to about 50:50; preferably 10:90 to about 40:60 and most preferably 20:80 to 40:60.

To produce the catalysis system, the Lewis acid, transition metal halide (if desired), Bronsted acid or Bronsted acid donor, (first) fluid hydrocarbon and inert solvent (where present) may be combined at supercritical conditions and within the above ranges of concentration in a catalyst formation reactor. Thus, the catalyst may be produced by contacting the preferred Lewis acid, $AlCl_3$, the preferred transition metal chloride (either zirconium or copper), and a supercritical fluid comprising a (first) fluid hydrocarbon, preferably a $C_6$–$C_{12}$ n- or i-alkane, and an inert solvent, preferably ethane or propane, most preferably propane, in the ratio of from about 20:80 to about 30:70, and a Bronsted acid, preferably HCl, or Bronsted acid donor, RX, at about 1000 psi and 400° F. (205° C.). The Bronsted acid is preferably added after the stream contacts the Lewis acid.

If a Bronsted acid is present during the contact of the (first) fluid hydrocarbon with solid Lewis acid, the contact time with the solid Lewis acid should be limited to a time sufficient to produce the discrete catalyst complex. The (second) hydrocarbon is then added to constitute the catalysis system.

Thus, in a preferred continuous process of forming the catalyst, the fluid hydrocarbon mixture comprising the $C_2$–$C_{14}$ alkane and inert solvent would desirably flow over a surface that presents the Lewis acid and transition metal halide to the flowing supercritical fluid mixture in a catalyst formation reactor. The mixture's flow rate may then be adjusted such that the fluid is not in contact with the Lewis acid for more than about 10 minutes, preferably less than about 5 minutes, and most preferably less than about 3 minutes. The optimum residence time range will depend upon the specific (first) fluid hydrocarbon and the temperature and pressure conditions. The Bronsted acid or Bronsted acid donor is then added.

It should be noted that for as long as the supercritical mixture of (first) fluid hydrocarbon comprising $C_2$–$C_{14}$ alkane and solvent and Bronsted acid is in contact with a solid Lewis acid of the metal halide-type, oligomerization of the hydrocarbon chains may continue. By taking the supercritical fluid out of contact with the solid Lewis acid, the desired catalyst complex may be obtained that is active and selective for the cracking of hydrocarbon feedstocks.

Liquid Phase Operation

In liquid phase operation the catalyst may be conveniently prepared by dissolving the Lewis acid in the (first) fluid hydrocarbon and thereafter, based upon the content of dissolved Lewis acid, adding appropriate quantities of Bronsted acid halide or Bronsted acid donor to the liquid.

Alternatively, the Lewis acid-fluid hydrocarbon solution may be added to the reactor. The Bronsted acid halide or donor is then added to the hydrocracking reactor such that the catalyst forms in the homogenous mixture in the reactor prior to dilution of the catalyst complex with the (second) fluid hydrocarbon and prior to addition of the feedstock and hydrogen.

However formed, the catalyst complex is dissolved in the total non-reacted hydrocarbon in an amount that provides a catalyst complex concentration of from about 5.0 to about 40 millimoles per 1000 g of total non-reacted hydrocarbon, measured as $MX_m$ where M is a Group 3a, 5a or 5b metal or metalloid, X is halide and "m" is an integer equal to the highest oxidation state of M. The homogenous fluid medium is maintained at a temperature sufficient to prevent precipitation of the catalyst complex from the catalysis system.

The Invention Processes

Hydrocracking occurs readily when the feedstock is contacted with the catalysis system. This contacting may take place in a continuous flow reactor, for example a continuous stirred reactor.

The proportion of hydrocarbon feedstock:catalysis system (wt/wt) supplied to the reactor may be in the ratio from about 1:1 to about 1:20. Preferably, the ratio should be from about 1:2 to about 1:10, most preferably about 1:2.

Residence time of the catalysis system with feedstock in the reactor depends on the feedstock, but should be at least about 20 minutes, preferably at least about 40 minutes, to achieve a useful conversion to desired products.

Conversion of feedstock to lower molecular weight hydrocarbons is high and, depending upon the particular catalyst complex used, and the constituency of the total non-reacted hydrocarbon and feedstock, ranges up to 95–100% in a single pass. Thus, for a stream of hexadecane in the presence of a catalysis system obtained from the $AlCl_3/HCl$ acid pair or $AlCl_3/RX$ pair and normal heptane, reaction with hydrogen can provide conversion of hexadecane of up to about 99% in a single pass.

Upon completion of the process the separation of catalyst complex from the total non-reacted hydrocarbon may be readily accomplished. The total non-reacted hydrocarbon may be separated from the catalyst complex by flashing or by subjecting the catalyst system to an absorbent for the catalyst complex. Alternatively, the catalyst complex may be precipitated from the total non-reacted hydrocarbon by reducing the temperature. The recovered catalyst may be treated with $H_2$ over a suitable catalyst to regenerate the Lewis acid which may then be used to prepare fresh charges of the catalysis system.

Supercritical Fluid Operation

In the practice of the process with a supercritical fluid medium, the (second) fluid hydrocarbon (and optional inert solvent) is first charged to the reactor and maintained at conditions so that its contents are in a supercritical fluid state. The catalyst complex is then charged to the reactor. Typically, the concentration of catalyst complex is maintained within the reactor to be between about 5 to about 50, preferably between about 10 to about 40, expressed as millimoles of Lewis acid/1000 g of total non-reacted hydrocarbon. Preferably about 30 millimoles of catalyst complex per 1000 g of weight of total non-reacted hydrocarbon is maintained to achieve commercially useful reaction rates.

Hydrocarbon feedstock is then charged to the reactor. When the total non-reacted hydrocarbon contains an inert solvent, the ratio of $C_2$–$C_{14}$ alkane:inert solvent in the reactor is preferably in the range 20:80 to 30:70, although other ratios may also be used, as long as supercritical fluid conditions are maintained.

While charging the (first) hydrocarbon to the reactor, a controlled quantity of Bronsted acid or Bronsted acid donor should be injected into the reactor upstream of the feedstock addition in order to provide a proportion of the acid or donor ranging from about 0.5 to about 1.5, and preferably about 1.0 to about 1.5, expressed as a molar ratio relative to the Lewis acid. Hydrogen flow is generally maintained to be between 5 and 15 times the molar flow rate of the feedstock.

Alternatively, the catalyst complex may be first produced in the formation reactor. This catalyst composition may then be injected into the reactor, subsequent to dilution, into which the feedstock and hydrogen are charged.

In the reactor all components of the catalysis system plus dissolved $H_2$ become the homogenous medium. The feedstock may or may not be dissolved in the homogeneous medium depending on its molecular weight.

The rate of feedstream introduced into the reactor relative to the catalysis system on a weight basis should generally be between 0.5 and 1.0. While residence times in the reactor will depend on many factors including amount of catalyst, acid-pair of catalyst, type of feedstock, and desired single-pass conversion, the hydrocarbon feedstock should typically have a residence time sufficient to achieve a conversion approaching 100%. This residence time should be at least about 5 minutes, preferably at least 8 minutes, and most preferably at least 10 minutes. Thus, the breakdown of high molecular weight to low molecular weight hydrocarbons takes place in a relatively short time. Typical conversions can range up to 100% conversion on a single pass through the reactor depending upon reactor conditions, actual catalyst used and the hydrocarbon feedstock.

The temperature within the hydrocracking reactor is maintained between about 400° and about 1,100° F., preferably between 500° and 800° F. The pressure is maintained below 1,000 psi; preferably between from about 450 to about 700 psi.

If the pressure in the reactor is dropped to below the pressure required to maintain supercritical fluid conditions, the catalyst is no longer soluble in the fluid hydrocarbon such that discrete catalyst complex particles will precipitate from the catalysis system. Therefore, it is desirable that precautions be taken to excessive pressure drops.

The components of the effluent stream from the hydrocracking reactor including product, catalyst complex, fluid hydrocarbon (with optional solvent) and any excess Bronsted acid. The catalyst complex is readily precipitated by reducing the pressure to subcritical ranges. The residual non-separated feedstock is then recycled back to the reactor inlet as is the total non-reacted hydrocarbon. The products may be diverted for other use.

Liquid Phase Operation

In liquid phase operation, the homogenous catalysis system is formed by dissolving a quantity of Lewis acid in the (first) fluid hydrocarbon while simultaneously or subsequently adding in appropriate quantities of the Bronsted acid or Bronsted acid donor to the medium and, if desired, a transition metal halide. This homogeneous medium is maintained in a reaction zone at a temperature of at least about 430° F., and preferably from about 450° F. to about 850° F., and a pressure of from about 500 to about 650 psia. The catalyst complex is then diluted by the addition of the (second) fluid hydrocarbon.

The hydrocarbon feedstream and hydrogen are then introduced and the stated temperature and pressure are maintained for a time sufficient to achieve the desired hydrocrackate product.

Contact of the catalysis system with the feedstock should be such as to provide a weight ratio of catalysis system to feedstock of from about 1:1 to about 2:1 by weight. Hydrogen is normally directly fed into the reactor at 5–15 times the molar feed rate of the feedstock. Residence time of the feedstock within the reaction zone is preferably long enough to permit complete reaction of the quantity of feedstock admitted to the zone. Generally the residence time of the hydrocarbon feedstock in the reaction zone should be at least about 20 minutes, preferably at least about 40 minutes. Following the reaction, the catalyst complex is separated from the lower molecular weight products by flashing or by running the reaction medium through a bed of absorbent for the catalyst complex after reducing the temperature of the medium. (A bed of gamma or eta alumina may serve as an absorbent for the catalyst complex.) Alternatively, the catalyst complex may be precipitated from the reaction medium by reducing the temperature. The catalyst complex can then be sent to a separate reactor for conversion of the catalyst complex to the Lewis acid for reuse.

As explained above, the hydrocrackate contains the desired low molecular weight products together with the catalysis system and any excess Bronsted acid. Since the catalysis system is highly active for cracking, it is advantageous to remove the catalysis system from the effluent product as soon as it leaves the reactor.

Figure 1:
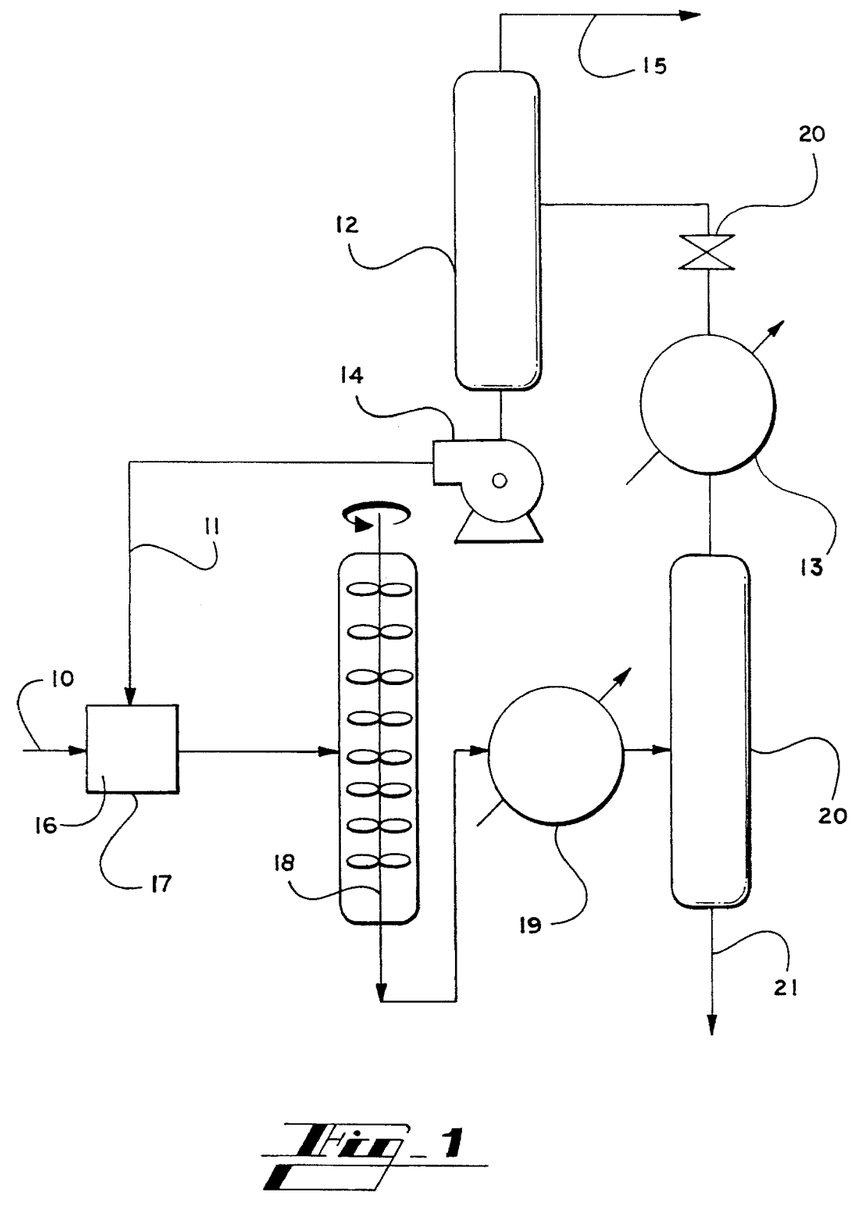
FIG. 1 is a flow diagram of the hydrocracking process of this invention employing a catalysis system in the supercritical state.

FIG. 1 is an illustration of the hydrocracking process of this invention wherein the catalysis system is in the supercritical state. For purposes of discussion, the feedstock is stated to be a deasphalted oil; although, the flow chart is equally applicable for other pretreated feedstocks. Prior to entry into the hydrocracking reactor, the feedstock is deasphalted wherein refractory asphaltenes and metals are concentrated and forwarded, as a byproduct stream, to gasification to produce energy and ash. Thus, the quality of deasphalted oil sent to the hydrocracking reactor is maximized. Methods of deasphalting crude feedstocks are known in the art and include the ROSE® processes of Kerr-McGee Corporation. See, for instance, U.S. Pat. Nos. 4,125,409, 4,239,616 and 4,273,644, herein incorporated by reference. Such processes principally rid heavy crude of polynuclear-aromatic compounds and metals.

As set forth in FIG. 1, the deasphalted oil enters the mixer 16 at 10 and is joined with the catalysis system from flash tower 12. The homogenous catalysis system containing metal halide Lewis acid catalyst dissolved in the fluid hydrocarbon is fed from flash tower 12 to pump 14. The catalysis system is then charged from the outlet of pump 14 to mixer 16. Optionally, make-up catalysis system 11 may combine with the stream exiting pump 14 and enter mixer 16. A hydrogen steam 17 further enters mixer 16 and combines with the deasphalted oil and catalysis system. The deasphalted oil and catalysis system (along with hydrogen) is then charged into reactor 18. Reactor 18 is provided with agitation such that the feedstock and catalysis system (which may be immiscible) are well mixed. Hydrocracking occurs leading to hydrocrackate which is at least partially soluble in the catalysis system. The product then exits reactor 18 and enters heater 19. Here, the mixture is heated above the critical temperature and critical pressure of the fluid hydrocarbon in the catalysis system. Separation of the hydrocrackate and unreacted feed from the catalysis system (due to differences in density) occurs in separator 20. A portion of hydrocrackate, unreacted feed and high molecular weight by-products 21 leave through the bottom of separator 20. The supercritical phase containing the remaining hydrocrackate, unreacted hydrogen, catalyst and light hydrocarbons are then transported to heat exchanger 13 wherein the temperature is decreased. The pressure is reduced across valve 20. The mixture is sent to flash drum 12. The supercritical fluid returns to a liquid state in tower 12. The fluid hydrocarbon and dissolved catalyst exits tower 12 and is transferred to mixer 16 via pump 14. Light hydrocarbons, including a portion of the desired hydrocrackate, with other impurities such as $H_2S$, as well as dissolved hydrogen leave tower 12 at 15 as a vapor phase.

Figure 2:
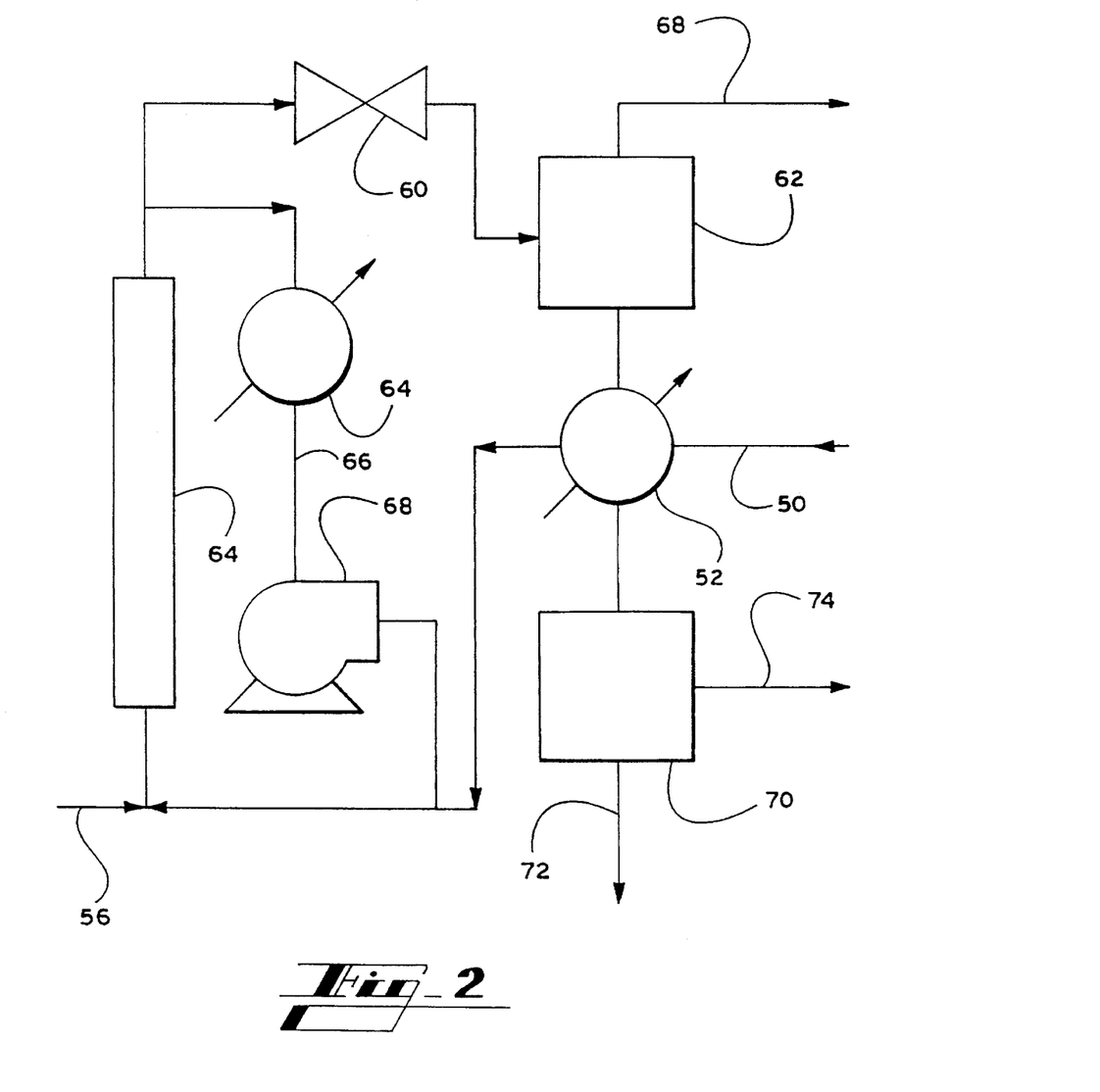
FIG. 2 shows an alternative flow diagram of the hydrocracking process of this invention which use a catalysis system in the liquid state.

FIG. 2 is an illustration of the hydrocracking process wherein the catalysis system is in a liquid state. Excellent results with heavy paraffinic feedstreams have been obtained using the flow scheme set forth in FIG. 2. (The scheme of FIG. 2 is, however, also applicable for use with other feedstreams.) As set forth in FIG. 2, where the feedstock consists principally of mixed paraffins, the feedstock enters the system at 50 and is heat exchanged with the hydrocrackate at heat exchanger 52 and sent to autoclave reactor 54. Hydrogen is fed into the autoclave 54 through line 56. (To minimize the formation of "hydrogen bubbles" in the reactor, the reactor may first be filled with the feedstream and catalysis system while the system is brought to operating conditions. A hydrogen feedstream is then introduced.) Mixing of the feedstock, catalysis system and hydrogen is promoted within autoclave 54. Hydrocrackate and the catalysis system are withdrawn from autoclave 54 and pass through pressure let-down valve 60 into flash drum 62. A portion of the liquid stream consisting of the catalysis system and hydrocrackate exits autoclave 54 and enters heat exchanger 64, wherein the hydrocrackate and catalysis system is cooled. Cooling is necessary in order to remove the heat of reaction from the autoclave 54. The cooled stream is then reintroduced into autoclave 54 through recycle pump 58. Recycle pump 58 adjusts holding time such that 100% conversion of feedstock may be better obtained. Further, fresh catalysis system is introduced into the reactor at 66. Light ends, containing a portion of the desired hydrocrackate, pass overhead and exit flash drum 62 at 68 while the underflow from flash drum 62 passes to heat exchanger 52. The underflow is heat exchanged against the incoming feedstock 50. The cooled hydrocrackate and catalysis system pass to coalescer 70 in which the catalyst precipitates to form a separate phase. The catalyst residue passes on to reclamation at 72. Clarified hydrocrackate with non-reactive hydrocarbon 74 is then sent to final treatment steps, such as distillation and caustic scrubbing. Catalyst may be reclaimed in a separate hydrocracking step utilizing a suitable catalyst to regenerate the Lewis acid.

The design of the hydrocracking reactor is essentially only restricted by the functions that it is required to perform. For example, the reactor must be capable of withstanding the reaction conditions employed. Further, the reactor should be of such a design as to facilitate removal of the heat of reaction.

A preferred embodiment of this invention is the hydrocracking of feedstreams containing mixed paraffins. Such streams are obtained from distillates and lube oil feeds by freezing or chilling the crude and then filtering the mixed heavy paraffins therefrom. Such processes of dewaxing crude feedstreams are well known in the art. Illustrative results are represented with the use of a cetane feedstock and hexane as fluid hydrocarbon. Such feedstocks may be hydrocracked at temperatures between 400° and 460° F. and at pressures approximating 650 psig while employing a holding time of between about 20 to about 40 minutes. (As used herein, the term "holding time" is determined by dividing the volume of the reactor by the volumetric feed rate.) Almost total conversion may be achieved at such conditions. Further, the $C_3$–$C_5$ byproduct gas (typically 20 to 50 weight percent in the hydrocracking processes of the prior art) is considerably lower in the invention process.

It has been demonstrated that the hydrocrackate emulates the $C_2$–$C_{14}$ fluid hydrocarbon alkane used as the second hydrocarbon of the catalysis system. In other words, the hydrocrackate typically contains the same number of carbon atoms as the alkane employed as (second) hydrocarbon. For example, where the (second) hydrocarbon is 90 weight percent n-hexane and 10 weight percent n-heptane, the solvent/feedstock weight ratio being about 2:1, the hydrocrackate (from which the solvent has been subtracted) will contain approximately 90 to 94 weight percent hexane with virtually all of the remainder being heptane. The hydrocrackate is virtually free of heavy ends.

While the simplified flow diagram of FIGS. 1 and 2 show basic flow schemes, those of ordinary skill in the art will readily appreciate the additional equipment and modifications that may be necessary in practice.

The following examples are illustrative of the invention and do not in any way limit or define the scope of the invention.

EXAMPLES

The examples follow the flow scheme set forth in FIG. 2, as discussed above, except that recycle pump 58 and external heat exchanger 64 were not employed. The autoclave was maintained at reaction temperature by a heating element. Further, subsequent to the exit of hydrocrackate 74 from coalescer 70, hydrocrackate 74 was transferred to a cold finger collection trap (chilled condenser) to verify that all of the hydrocrackate, including the light fragments, was collected.

Examples 1–9

An alkylaluminum chloride catalysis system was prepared by flowing 14.6 cc/hr of hexane through a bed initially containing 12 g of $AlCl_3$ at 200° F. To the resulting solution, containing about 1.6 wt.% $AlCl_3$ was added 5.6 cc/hr of hexane containing 2.78 wt.% butyl chloride. The mol ratio of butyl chloride:$AlCl_3$ was approximately 1:1 in Examples 1, 2 and 4–9 and 1.4:1 in Example 3. The resulting catalysis system containing about 7,000 mol ppm of the catalyst complex was then flowed with hydrogen (10–15 SL/Hr) into a stirred autoclave. A separate stream of cetane ($C_{16}H_{34}$) was fed to the autoclave at 9.4 cc/hr. The weight ratio of hexane to cetane was 2/1. The temperature within the autoclave was maintained at selected levels between 400° and 460° F. The operating pressure was 650 psig and the holding time was 40 minutes. The hydrocrackate and catalysis system were then subjected to the conditions described above under the discussion of FIG. 3. Since the mass flow rates of solvent (hexane) and reactant (cetane) are known the product can be expressed on a solvent-free basis by mathematically subtracting the solvent from the total product. Independent studies showed that there was no hydrocracking of the hexane at the conditions tested. The results, expressed on a solvent-free basis, are set forth in the Table below:

$AlCl_3$ ratio was increased from 1 (Example 1) to 1.4 (Example 3). The cetane conversion dropped and the production of light gases ($C_3$–$C_5$) increased in Example 3. This illustrates the importance of limiting the amount of Bronsted acid relative to the Lewis acid.

Example 10

An alkylaluminum chloride catalyst was prepared by flowing hexane (17 cc/hr) through a bed of aluminum trichloride at 200° F. to produce a stream containing about 1.6% $AlCl_3$. To the resulting solution containing dissolved catalyst precursor was added an additional supply of hexane (9.4 cc/hr) containing chlorobutane. The resulting catalysis system was then charged to a stirred autoclave with about 11 cc/hr of hexadecane. The weight ratio of hexane to hexadecane was about 2:1. No hydrogen was added to the system. The temperature was increased to about 430° F. and the pressure increased to about 630 psig. The reaction was allowed to occur for about 90 minutes. Only 0.14 liters of off gas was observed during a one hour material balance. Product liquid analysis, when compared with the composite feed suggested very little reaction had taken place.

| Carbon No. | Product (MOL %) | Feed (MOL %) |
| --- | --- | --- |
| $C_4$ | 0.069 | 0.619 |
| $C_5$ | 0.507 | 0.141 |
| $C_6$ | 71.518 | 73.985 |
| $C_7$ | 7.874 | 6.788 |
| $C_8$ | 0.127 | 0.112 |
| $C_{12}$ | 0.023 | |
| $C_{13}$ | | 0.050 |
| $C_{14}$ | 0.322 | |
| $C_{16}$ | 19.305 | 18.292 |
| $C_{20}$ | 0.196 | |

| | 1 | 2 | 3 | 4 | 5 | 6 | 7 | 8 | 9 |
| --- | --- | --- | --- | --- | --- | --- | --- | --- | --- |
| $C_{16}$ Conv. % | 100 | 100 | 56 | 100 | 100 | 66 | 99 | 76 | 71 |
| T(°F.) | 465 | 460 | 458 | 431 | 430 | 420 | 400 | 400 | 401 |
| $C_6$–$C_9$ Distribution, wt. % | | | | | | | | | |
| i-$C_6$ | 38.65 | 54.31 | 60.93 | 38.91 | 47.52 | 46.63 | 28.28 | 38.21 | 40.04 |
| n-$C_6$ | 52.56 | 35.65 | 32.40 | 51.16 | 46.03 | 47.70 | 62.59 | 51.56 | 49.71 |
| $C_7$ | 7.35 | 9.60 | 3.99 | 9.29 | 5.74 | 1.77 | 8.03 | 7.46 | 7.33 |
| $C_8$ | 1.07 | 0.40 | 2.11 | 0.53 | 0.66 | 2.02 | 0.78 | 1.86 | 1.96 |
| $C_9$ | 0.38 | 0.05 | 0.57 | 0.13 | 0.06 | 1.90 | 0.31 | 0.92 | 0.97 |
| $\Sigma(C_6 + C_7)$ | 98.56 | 99.55 | 97.33 | 99.35 | 99.29 | 96.10 | 98.90 | 97.23 | 97.06 |
| Byproducts | | | | | | | | | |
| $C_3$–$C_5$ (wt %) | 6.36 | 2.40 | 23.86 | 2.18 | 7.68 | 17.89 | 5.39 | 5.73 | 7.29 |
| $C_4/C_5$ (wt) | 0.74 | 1.80 | 1.40 | 1.70 | 2.90 | 1.80 | 1.50 | 1.50 | 1.10 |
| $C_9^+$ | 0.17 | 0.00 | 0.00 | 0.00 | 0.00 | 1.00 | 0.00 | 0.24 | 0.25 |
| Iso/Normal | | | | | | | | | |
| $C_4$ | 1.70 | 5.30 | 3.50 | 3.30 | 1.50 | 2.00 | 3.50 | 6.90 | 6.60 |
| $C_5$ | 7.30 | 14.10 | 13.10 | 19.00 | 12.40 | 10.90 | 14.30 | 19.80 | 24.90 |
| $C_6$ | 0.74 | 1.50 | 1.90 | 0.80 | 1.00 | 1.00 | 0.50 | 0.70 | 0.80 |

In all cases, the $C_6$–$C_9$ liquid product is greater than 95% $C_6$–$C_7$. The i/n ratio of the $C_4$ and $C_5$ is greater than that corresponding to equilibrium at the reaction temperature, suggesting that the iso form is the predominant product. The $C_7$ fraction is totally isoheptane. The conditions for examples 1 and 3 are identical except that the butyl chloride/

Example 11

To the reactor of Example 10, hydrogen was introduced at about 5 SL/hr over a two hour period. The product was predominantly i-hexane as reflected in the Table below:

| Carbon No. | Product (MOL %) | Feed (MOL %) |
|---|---|---|
| $C_3$ | | 0.013 |
| $C_4$ | 0.227 | 0.633 |
| $C_5$ | 0.192 | 0.145 |
| i-$C_6$ | 17.018 | 6.095 |
| n-$C_6$ | 73.722 | 69.561 |
| $C_7$ | 8.780 | 6.942 |
| $C_8$ | 0.061 | 0.114 |
| $C_{9+}$ | | 0.051 |
| $C_{16}$ | | 16.440 |

These results demonstrate that hydrocracking of cetane took place when $H_2$ was added to the system and that the product was predominantly i-hexane.

Example 12

The experimental procedures set forth in Examples 1–9 above were followed to prepare 6,000 mol ppm of the catalyst complex (activated with chlorobutane) dissolved in heptane. A stream of hexadecane was added to give a composite feed containing one-third hexadecane and two-thirds heptane (by weight). This was charged, together with hydrogen, to a Parr stirred autoclave. The operating conditions were 650 psig, 460° F., with a holding time of 40 minutes. Total product (less the unconverted hydrogen) was collected during a two-hour material balance period. The material balance was excellent (98.3%). A sample of the product was submitted for GC analysis. The cetane conversion was 84%. The solvent (99.4% pure heptane containing 97.7% n-heptane) was mathematically subtracted from the product to obtain the actual solvent-free hydrocrackate composition. The product contained 85% heptane, 90% of which was n-heptane. An analysis (on a cetane-free basis) is listed in the table below:

| Component | Weight Percent |
|---|---|
| $C_3$ | 1.01 |
| $C_4$ | 5.07 |
| $C_5$ | 2.60 |
| $C_6$ | 6.41 |
| i-$C_7$ | 10.16 |
| n-$C_7$ | 74.51 |
| $C_8$ | 0.01 |
| $C_9$ | 0.11 |
| $C_{10}$ | 0.12 |

I claim:

1. A method of hydrocracking a high molecular weight hydrocarbon feedstock into lower molecular weight components comprising the steps of:
    (1) forming a catalyst complex comprising the product of reaction of
        (a) a Lewis acid of the formula $R_{(m-2-z)}MX_{2+z}$ wherein M is aluminum or boron, X is a halide, R is a hydrocarbyl radical having 1 to 12 carbon atoms, "m" is an integer equal to the greatest oxidation state of M, and "z" is an integer of 0, 1 or m−2;
        (c) a hydrogen halide which upon addition to the solution forms a catalyst complex;
        (b) a paraffinic hydrocarbon having from about six to about fourteen carbon atoms, said paraffinic hydrocarbon being in an amount sufficient to form a solution with the Lewis acid; and
    (2) adding an amount of said paraffinic hydrocarbon sufficient to solubilize said catalyst complex to thereby form a catalysis system wherein the concentration of catalyst complex is maintained between from about 5.0 to about 50 millimoles of Lewis acid per 1,000 grams of said non-complexed paraffin hydrocarbon;
    (3) adding hydrogen and the feedstock to the catalysis system while maintaining the catalysis system at a temperature such that the catalyst complex does not precipitate for a time sufficient in order for hydrocracking to occur in a homogeneous solution of the feedstock and catalysis system; and
    (4) separating the lower molecular weight components of the hydrocracked product from the catalyst complex.

2. The method of claim 1, wherein the feedstock is deasphalted oil or a mixture comprising paraffin hydrocarbons containing from about 14 to about 35 carbon atoms.

3. The method of claim 2, wherein X is chloride or bromide and the hydrogen halide is HCl or HBr.

4. The method of claim 3, wherein the hydrogen halide is HCl and is the decomposition product of alkyl chloride.

5. The method of claim 2, wherein the Lewis acid is $AlCl_3$.

6. The method of claim 2, wherein the catalysis system is maintained in step (2) above both its critical temperature and critical pressure.

7. The method of claim 6, wherein X is chloride or bromide and the hydrogen halide is HCl or HBr.

8. The method of claim 6, wherein the catalysis system further contains a solvent selected from the group consisting of methane, ethane, propane, sulfur dioxide, nitrogen oxides, low molecular weight halocarbons, rare earth gases, and carbon dioxide.

9. The method of claim 8, wherein the solvent is selected from methane, ethane or propane.

10. The method of claim 2, wherein the feedstock is a mixture comprising paraffin hydrocarbons and further wherein the carbon number lower molecular weight components of said hydrocracked product is equivalent to carbon number of said the paraffinic hydrocarbon.

11. The method of claim 2, wherein the feedstock is maintained at a temperature of from about 200° to about 430° C. and under a pressure sufficient to maintain the catalysis system and the feedstock in step (2) in a liquid state.

12. The method of claim 3, wherein the Lewis acid is $R_{1-z}AlCl_{2+x}$ and the hydrogen halide is HCl.

13. The method of claim 12, wherein the Lewis acid is $AlCl_3$.

14. The method of claim 1, wherein the Lewis acid is $R_{1-z}AlCl_{2+z}$ and the hydrogen halide is HCl.

15. The method of claim 1, wherein the molar ratio of hydrogen halide and said paraffinic hydrocarbon in the catalyst complex is between from about 0.5 to about 1.5.

* * * * *